(12) United States Patent
Lepri et al.

(10) Patent No.: US 11,746,076 B2
(45) Date of Patent: Sep. 5, 2023

(54) PROCESS FOR METHANOL PRODUCTION

(71) Applicant: CASALE SA, Lugano (CH)

(72) Inventors: Maddalena Lepri, Cavallasca (IT); Pietro Moreo, Lugano (CH); Raffaele Ostuni, Lugano (CH)

(73) Assignee: CASALE SA, Lugano (CH)

( * ) Notice: Subject to any disclaimer, the term of this patent is extended or adjusted under 35 U.S.C. 154(b) by 0 days.

(21) Appl. No.: 16/486,982

(22) PCT Filed: Jan. 31, 2018

(86) PCT No.: PCT/EP2018/052355
§ 371 (c)(1),
(2) Date: Aug. 19, 2019

(87) PCT Pub. No.: WO2018/153625
PCT Pub. Date: Aug. 30, 2018

(65) Prior Publication Data
US 2021/0130272 A1 May 6, 2021

(30) Foreign Application Priority Data
Feb. 23, 2017 (EP) .................................. 17157696

(51) Int. Cl.
*C07C 29/151* (2006.01)
*C07C 31/04* (2006.01)

(52) U.S. Cl.
CPC .......... *C07C 31/04* (2013.01); *C07C 29/1518* (2013.01)

(58) Field of Classification Search
None
See application file for complete search history.

(56) References Cited

U.S. PATENT DOCUMENTS

| 2003/0153632 A1* | 8/2003 | Wang ...................... C10G 2/32 |
| | | 518/703 |
| 2009/0018220 A1* | 1/2009 | Fitzpatrick .............. C12C 11/02 |
| | | 518/700 |
| 2015/0251983 A1 | 9/2015 | Panza et al. |

FOREIGN PATENT DOCUMENTS

| CA | 2213025 C | * 6/2006 | ......... C07C 29/1518 |
| EP | 0839786 A2 | 5/1998 | |
| WO | 2005108336 A1 | 11/2005 | |

(Continued)

OTHER PUBLICATIONS

International Preliminary Report on Patentability for International Application No. PCT/EP2018/052355 completed Feb. 11, 2019.

(Continued)

*Primary Examiner* — Medhanit W Bahta
(74) *Attorney, Agent, or Firm* — Dorsey & Whitney LLP

(57) ABSTRACT

Process for the synthesis of methanol comprising: reforming a hydrocarbon feedstock into a synthesis gas containing carbon oxides and hydrogen in a molar ratio $(H_2-CO_2)/(CO+CO_2)$ lower than 1.7; elevating said molar ratio to a value of at least 1.9; compressing said synthesis gas and converting the same into crude methanol; separating said crude methanol into a liquid stream of methanol and a gaseous stream containing unreacted synthesis gas; subjecting at least 50% (vol) of said gaseous stream to hydrogen recovery and mixing the recovered hydrogen with said synthesis gas in order to elevate its molar ratio to a value of at least 1.9.

19 Claims, 1 Drawing Sheet

(56) References Cited

FOREIGN PATENT DOCUMENTS

| WO | 2006126017 | A1 | | 11/2006 | | |
|---|---|---|---|---|---|---|
| WO | 2008010743 | A1 | | 1/2008 | | |
| WO | WO-2017157530 | A1 | * | 9/2017 | ........... | B01D 53/229 |

OTHER PUBLICATIONS

International Search Report from International Application No. PCT/EP2018/052355 dated Apr. 30, 2018.

* cited by examiner

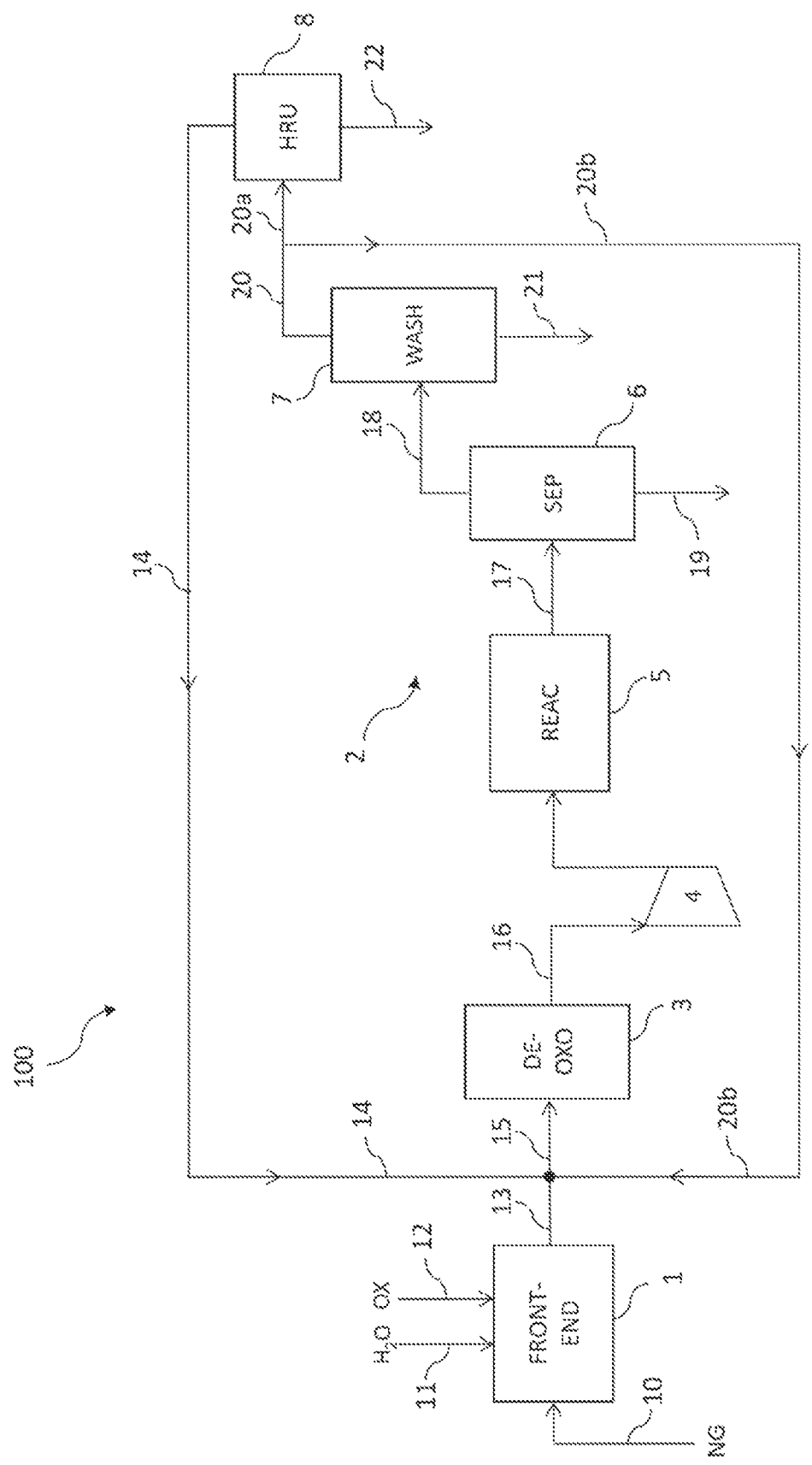

PROCESS FOR METHANOL PRODUCTION

FIELD OF APPLICATION

The present invention relates to a process and plant for the synthesis of methanol.

PRIOR ART

A process for the synthesis of methanol basically comprises the production of a make-up synthesis gas containing carbon oxides (CO, $CO_2$) and hydrogen ($H_2$) by means of reforming or partial oxidation of a hydrocarbon feedstock in a front-end section, and the conversion of said make-up synthesis gas into methanol in a synthesis loop.

The conversion of the make-up gas into methanol is carried out at high temperature (200-300° C.) and pressure (50-150 bar), in the presence of an appropriate catalyst, and involves the following reactions of hydrogenation of carbon oxides (CO, $CO_2$) and reversed water-gas shift:

$$CO + 2H_2 \leftrightarrows CH_3OH \quad \Delta H^0_{298} = -90.8 \text{ kJ/mol}$$

$$CO_2 + 3H_2 \leftrightarrows CH_3OH + H_2O \quad \Delta H^0_{298} = -49.6 \text{ kJ/mol}$$

$$CO_2 + H_2 \leftrightarrows CO + H_2O \quad \Delta H^0_{298} = +41.1 \text{ kJ/mol}$$

The global process is exothermic and is typically performed in an isothermal converter.

Said reactions are characterized by unfavourable thermodynamic equilibrium conditions, and only a fraction of the make-up synthesis gas is converted into methanol per pass over the catalyst. A stream containing the unreacted gas is typically separated from the stream of raw methanol obtained by the make-up gas conversion, and is then split into a first portion which is recirculated into the synthesis loop for further reaction and a second portion which is continuously withdrawn from the synthesis loop to avoid accumulation of inert compounds mainly including methane, argon and nitrogen. Said second portion is also referred to as purge gas stream and is typically not greater than 5% (in volume) of the original gaseous stream, as this amount is typically sufficient to avoid inert build-up in the synthesis loop.

An optimum make-up synthesis gas is a mixture of carbon oxides and hydrogen with a stoichiometric number SN equal to or higher than 2, wherein:

$$SN = (H_2 - CO_2)/(CO + CO_2)$$

The higher the SN (i.e. the hydrogen content), the better is the carbon efficiency. As a consequence, a make-up gas with SN>2 is strongly desired for the conversion into methanol.

However, the gas obtained by reforming or partial oxidation of a hydrocarbon feedstock in the front-end section often has SN<2 and needs to be conditioned. The most common way to condition the synthesis gas in order to achieve the required SN is to add hydrogen withdrawn from the above mentioned purge gas by a membrane unit or a pressure swing adsorption (PSA) unit. However, due to the relatively small amount of purge gas (i.e. not greater than 5%), the available technologies are able to treat gas with SN only slightly lower than 2, for example with SN of 1.8-1.9.

An alternative solution provides to subject part of the reformed, or partially oxidized, gas with SN<2 to a dedicated treatment before it is supplied to the synthesis loop. This treatment usually contains a water gas shift process, wherein CO and $H_2O$ are converted into $CO_2$ and $H_2$, and a $CO_2$ removal process. However, this solution has some disadvantages, since it requires the installation of an additional section comprising a water gas shift unit (i.e. an additional catalytic reactor) and a $CO_2$ removal unit, and entails considerable cost and energy consumption, e.g. for regenerating the CO2 removal solution. An optimum make-up synthesis gas also has a very low content of oxygen and a low concentration of inerts, which are typically methane, argon and nitrogen. Oxygen entails deactivation of the methanol synthesis catalyst, hence a high content of oxygen in the make-up gas would require frequent replacement of catalyst, with disadvantages in terms of high capital costs and long plant downtime.

As to the inerts, a high concentration thereof would lower the partial pressure of the reactants and for this reason it is discouraged to use a make-up gas with high concentration of inert gases for the methanol synthesis.

However, gas streams with very low SN (e.g. even less than 1.5), high oxygen content and high concentration of inerts are available from many plants, e.g. as waste streams, and have had so far little use. Owing to the wide availability and the low cost of said gas streams, there is a great interest in processes for the synthesis of methanol starting from them. This need is particularly felt for the small scale methanol production.

SUMMARY OF THE INVENTION

The aim of the invention is to provide a process for the synthesis of methanol which is particularly suitable when the synthesis gas has a stoichiometric number ($H_2$—$CO_2$)/(CO+$CO_2$) lower than 1.7 and possibly containing significant amounts of oxygen and inerts, while using commercially available catalysts and a simple and inexpensive synthesis loop layout.

These aims are reached with a process for the synthesis of methanol from a hydrocarbon feedstock according to claim 1.

Said process comprises the following steps: conversion of a hydrocarbon feedstock, obtaining a synthesis gas; compressing said synthesis gas to a synthesis pressure; reacting said synthesis gas at said synthesis pressure, obtaining crude methanol; subjecting said crude methanol to separation, obtaining a liquid stream of methanol and unreacted synthesis gas; subjecting at least part of said unreacted synthesis gas to a hydrogen recovery step, wherein:

the synthesis gas obtained from said conversion step contains carbon oxides and hydrogen in a stoichiometric molar ratio ($H_2$—$CO_2$)/(CO+$CO_2$) lower than 1.7;

prior to said reacting step, said stoichiometric molar ratio ($H_2$—$CO_2$)/(CO+$CO_2$) is elevated to a value of at least 1.9 by mixing the synthesis gas with a hydrogen-containing stream obtained from said hydrogen recovery step, and the part of unreacted synthesis gas subjected to said hydrogen recovery step is at least 50% (vol) of the total amount of the unreacted synthesis gas obtained from said separation step.

Said step of conversion may include reforming and/or partial oxidation of said hydrocarbon feedstock.

For the sake of brevity, the stoichiometric molar ratio ($H_2$—$CO_2$)/(CO+$CO_2$) will be abbreviated as SN.

The synthesis gas obtained from said reforming step preferably has a SN not greater than 1.6, more preferably not greater than 1.5, even more preferably comprised between 1 and 1.5.

Preferably, the SN of the synthesis gas is elevated to a value higher than 1.9, more preferably to a value of at least 2, even more preferably to a value higher than 2. According to a preferred embodiment, the SN is elevated to a value comprised between 2.1 and 2.3.

Said compression step is preferably performed in a multi-stage compressor, and the SN elevation to the above value may take place at the suction- or delivery-side of said compressor or at an intermediate stage thereof. Hence, according to different embodiments, said hydrogen-containing stream mixes with the synthesis gas at the suction- or delivery-side of said compressor or at an intermediate stage thereof.

According to a preferred embodiment, the unreacted synthesis gas drawn off from said separation step splits into a first portion and a second portion. Said first portion is subjected to the hydrogen recovery step, while said second portion mixes with the synthesis gas, by-passing the hydrogen recovery step. Accordingly said second portion will be also referred to as "by-pass stream".

According to different embodiments, said by-pass stream is recycled at the suction- or delivery-side of said multi-stage compressor or at an intermediate stage thereof, wherein it mixes with the synthesis gas. Said by-pass stream is advantageously used to regulate the stoichiometric molar ratio $(H_2—CO_2)/(CO+CO_2)$ of the synthesis gas prior to said reacting step.

Preferably, said first portion is at least 70% (vol) of the total amount of the unreacted synthesis gas drawn off from said separation step, more preferably it ranges between 85 and 90% (vol) thereof. Accordingly, said second portion is preferably not greater than 30% (vol) of the total amount of the unreacted synthesis gas, more preferably it ranges between 10 and 15% (vol) thereof.

According to a preferred embodiment, the process according to the invention also comprises subjecting the synthesis gas to a step of de-oxidation in order to remove possible oxygen contained therein prior to said reacting step. Said step of de-oxidation is carried out in a so-called de-oxo reactor and preferably takes place prior to said compression step.

Preferably, said step of de-oxidation provides for the catalytic reaction of oxygen with the hydrogen contained in the synthesis gas, thus forming water and obtaining an oxygen-depleted synthesis gas.

More preferably, said step of de-oxidation provides for the selective reaction of oxygen with carbon monoxide (CO), thus forming carbon dioxide ($CO_2$) and obtaining an oxygen-depleted synthesis gas. This embodiment is more preferred because does not consume hydrogen, which is the limiting reagent.

Preferably, said oxygen-depleted synthesis gas contains less than 300 ppm of oxygen.

According to a particular embodiment, said hydrogen recovery step comprises a permeation process through a membrane permeable to hydrogen and impermeable to other gases, e.g. inerts.

Preferably, said membrane-based process is operated with a pressure drop of around 30-40 bar, which is similar to the pressure difference between the unreacted synthesis gas subjected to the hydrogen recovery step and the synthesis gas obtained from the conversion of said hydrocarbon feedstock, so that the hydrogen-containing stream advantageously mixes with the synthesis gas at the suction-side of the compressor. According to this embodiment, the by-pass stream is also preferably recycled at the suction-side of said compressor. Accordingly, the SN of the synthesis gas is elevated to the above value of at least 1.9 prior to said compression step.

According to the embodiment of the invention comprising said de-oxidation step, the hydrogen-containing stream and/or said by-pass stream preferably mixes with said stream of synthesis gas at the inlet of the de-oxo reactor, meaning that the SN of the synthesis gas is elevated to the above value even prior to the de-oxidation step itself.

Said embodiment is particularly advantageous because said hydrogen-containing stream and said by-pass stream guarantee the thermal control of said de-oxo reactor. Since commercially available de-oxidation catalysts are very prone to coking at temperatures above 400° C., the recycle of said hydrogen-containing stream and/or said by-pass stream at the de-oxo reactor inlet is advantageous to dilute the feed gas, hence not to exceed such temperature.

According to another embodiment of the invention, said hydrogen recovery step comprises a pressure swing adsorption (PSA) process. In this embodiment, the hydrogen-containing stream preferably mixes with the stream of synthesis gas at an intermediate stage of the multi-stage compressor, being it operated with a lower pressure drop than the above permeation process, and thus resulting in an energy saving. Preferably, said hydrogen-containing stream is recycled to such intermediate stage by using of a circulator compressor. This embodiment is very advantageous especially in the cases where no de-oxidation step is required.

Preferably, the process according to the invention further comprises subjecting the unreacted synthesis gas drawn off from the separation step to a water washing in order to remove possible traces of methanol prior to said hydrogen recovery step. Accordingly said further step of washing provides a methanol-depleted gaseous stream mainly containing unreacted synthesis gas which is directed to said hydrogen recovery step, and an aqueous stream containing traces of methanol.

Said process for the synthesis of methanol is particularly suitable to be performed on a small scale. The term "small scale" generally refers to a production of methanol in crude not greater than 100 MTPD (metric tons per day).

The main advantage of the present invention is that it allows using a synthesis gas which, for its particular characteristics, could not be acceptable for the prior art methanol processes, while using a synthesis loop with a simple design and a compact layout. In particular, the present invention allows using an effluent of the reforming process with the following characteristics: a stoichiometric number lower than 1.7, an oxygen content higher than 3% (vol), a content of inert compounds higher than 55% (vol).

The advantages of the invention will emerge even more clearly with the aid of the detailed description below relating to a preferred embodiment.

BRIEF DESCRIPTION OF THE DRAWING

FIGURE is a scheme of a plant for the synthesis of methanol, according to an embodiment of the invention.

DETAILED DESCRIPTION

FIGURE illustrates a block scheme of a plant 100 for the synthesis of methanol comprising a front-end section 1 and a synthesis loop 2.

The front-end section 1 produces a synthesis gas 15 which is subjected to de-oxidation in a de-oxo reactor 3, compressed in a multi-stage compressor 4 and subsequently reacted in the synthesis loop 2.

The front-end section 1 essentially comprises a conversion section, which could be a reforming section or a partial oxidation section.

The synthesis loop 2 comprises a block 5 essentially containing a catalytic reactor and a condensation section, a separator 6, a water washing column 7 and a membrane-based hydrogen recovery unit (HRU) 8. Said block 5 provides a stream 17 of crude methanol, which is supplied to the separator 6 which separates liquid methanol 19 from the bottom and unreacted synthesis gas 18 from the top. Said unreacted gas 18 is subjected to water washing in column 7 and the gaseous stream 20 drawn off from the top of the column 7 feeds the HRU 8 from which a hydrogen-containing stream 14 is released.

More in detail, the operation of the plant is the following.

A stream 10 of natural gas is supplied to the front-end section 1, wherein is reformed in the presence of steam 11 and oxygen 12 providing a synthesis gas 13. Said synthesis gas 13 contains carbon oxides (CO, $CO_2$) and hydrogen ($H_2$) with a low stoichiometric number $(H_2—CO_2)/(CO+CO_2)$ for example lower than 1.4, and further contains residual amounts of oxygen and inert gases.

Said synthesis gas 13 mixes with the above mentioned hydrogen-containing stream 14 and with a portion 20b of the effluent stream of the column 7, which adjust the stoichiometric number $(H_2—CO_2)/(CO+CO_2)$ to a value higher than 2, for example in the range 2.1 to 2.3.

The resulting synthesis gas 15 is sent to said de-oxo reactor 3, wherein said residual oxygen reacts with hydrogen to give water, thus obtaining an oxygen-depleted synthesis gas 16. The latter is then compressed to a synthesis pressure of about 40-100 bar within the multi-stage compressor 4.

The so-compressed gas is supplied to the synthesis block 5 of the loop 2, which provides a stream 17 of crude methanol. Said stream 17 subsequently enters the separator 6, which separates unreacted synthesis gas 18 from liquid methanol 19, as already explained above. Said liquid methanol 19 is subjected to purification in a suitable purification section (not shown), while the gaseous stream 18 enters the water washing in column 7, wherein traces of methanol are removed in an aqueous stream 21.

The resulting methanol-free stream 20 of unreacted synthesis gas splits into two portions; a first portion 20a feeds the hydrogen recovery unit 8 and the second portion 20b is recycled upstream of the de-oxo reactor 3.

Said hydrogen recovery unit 8 separates a tail-gas 22 containing inert components and the already mentioned hydrogen-containing stream 14. The latter is recycled upstream of the de-oxo reactor 3, wherein it mixes with the effluent 13 of the front-end section 1 and said second portion 20b of unreacted synthesis gas, forming the stream 15 of synthesis gas.

The invention claimed is:

1. A process for a synthesis of methanol from a hydrocarbon feedstock, the process comprising:
   converting said hydrocarbon feedstock, thereby obtaining an amount of a synthesis gas;
   compressing the amount of said synthesis gas to a synthesis pressure;
   reacting the amount of said synthesis gas at said synthesis pressure, thereby obtaining crude methanol;
   subjecting said crude methanol to separation, thereby obtaining a liquid stream of methanol and unreacted synthesis gas; and
   subjecting at least part of said unreacted synthesis gas to a hydrogen recovery step;
   wherein:
   the synthesis gas obtained from conversion of said hydrocarbon feedstock contains carbon oxides and hydrogen in a stoichiometric molar ratio $(H_2—CO_2)/(CO+CO_2)$ lower than 1.7;
   prior to said reacting step, said stoichiometric molar ratio $(H_2—CO_2)/(CO+CO_2)$ is elevated to a value of at least 1.9 by mixing the synthesis gas with a hydrogen-containing stream obtained from said hydrogen recovery step; and
   said part of unreacted synthesis gas subjected to said hydrogen recovery step is at least 50% (vol) of the total amount of the unreacted synthesis gas obtained from said separation step.

2. The process of claim 1, wherein the synthesis gas obtained from said reforming step has a stoichiometric molar ratio $(H_2—CO_2)/(CO+CO_2)$ not greater than 1.6.

3. The process of claim 2, wherein the stoichiometric molar ratio $(H_2—CO_2)/(CO+CO_2)$ is not greater than 1.5.

4. The process of claim 2, wherein the stoichiometric molar ratio $(H_2—CO_2)/(CO+CO_2)$ is between 1 and 1.5.

5. The process of claim 1, wherein prior to said reacting step said stoichiometric molar ratio $(H_2—CO_2)/(CO+CO_2)$ is elevated to a value of at least 2.

6. The process of claim 5, wherein the value is higher than 2.

7. The process of claim 5, wherein the value is between 2.1 and 2.3.

8. The process of claim 1, wherein said unreacted synthesis gas splits into a first portion that is subjected to said hydrogen recovery step, and a second portion that mixes with the synthesis gas prior to said reacting step.

9. The process of claim 1, further comprising de-oxidation prior to said compression step, wherein oxygen contained in said synthesis gas reacts with hydrogen to generate water, thereby obtaining an oxygen-depleted synthesis gas.

10. The process of claim 9, wherein said oxygen-depleted synthesis gas contains less than 300 ppm of oxygen.

11. The process of claim 1, wherein said hydrogen recovery step includes a permeation process through a membrane.

12. The process of claim 11, further comprising de-oxidation prior to said compression step, wherein said hydrogen-containing stream mixes with the synthesis gas prior to said step of de-oxidation.

13. The process of claim 12, further comprising splitting said unreacted synthesis gas into a first portion that is subjected to said hydrogen recovery step, and a second portion that mixes with the synthesis gas prior to said step of de-oxidation.

14. The process of claim 1, wherein said hydrogen recovery step includes a pressure swing adsorption process.

15. The process of claim 14, wherein said compression step being performed in a multi-stage compressor, wherein said hydrogen-containing stream mixes with the synthesis gas at an intermediate stage of said multi-stage compressor.

16. The process of claim 1, wherein the conversion of said hydrocarbon feedstock includes reforming and/or partial oxidation of said hydrocarbon feedstock.

17. The process of claim 1, further comprising subjecting the unreacted synthesis gas obtained from said separation step to a water washing in order to remove traces of methanol prior to said hydrogen recovery step.

18. The process of claim 1, which is suitable to be performed on a small scale.

19. The process of claim 8, wherein said first portion is at least about 70% (vol) of the total amount of the unreacted synthesis gas drawn off from said separation step, and said second portion is less than about 30% (vol) of the total amount of the unreacted synthesis gas.

* * * * *